(12) United States Patent
Chung et al.

(10) Patent No.: US 10,444,208 B2
(45) Date of Patent: Oct. 15, 2019

(54) METHOD FOR MEASURING THE CONCENTRATION OF A CHEMICAL SPECIES USING A REAGENT BASELINE

(71) Applicant: Myron L Company, Carlsbad, CA (US)

(72) Inventors: Russell Chung, Carlsbad, CA (US); Hirak T Chavda, San Marcos, CA (US); Guoliang Xiao, Carlsbad, CA (US)

( * ) Notice: Subject to any disclaimer, the term of this patent is extended or adjusted under 35 U.S.C. 154(b) by 160 days.

(21) Appl. No.: 15/625,720

(22) Filed: Jun. 16, 2017

(65) Prior Publication Data
US 2017/0363593 A1 Dec. 21, 2017

Related U.S. Application Data

(60) Provisional application No. 62/351,671, filed on Jun. 17, 2016.

(51) Int. Cl.
*G01N 31/00* (2006.01)
*G01N 33/18* (2006.01)
*G01N 27/416* (2006.01)

(52) U.S. Cl.
CPC .......... *G01N 31/005* (2013.01); *G01N 33/18* (2013.01); *G01N 27/4168* (2013.01)

(58) Field of Classification Search
CPC .............. G01N 27/02; G01N 27/3276; G01N 33/5438; G01N 31/005; G01N 33/18; G01N 27/4168; C12Q 1/004
See application file for complete search history.

(56) References Cited

U.S. PATENT DOCUMENTS

| | | |
|---|---|---|
| 6,177,260 B1 | 1/2001 | Benzi et al. |
| 2004/0245121 A1 | 12/2004 | Nagakawa |
| 2010/0033160 A1* | 2/2010 | Kocherginsky .... G01N 27/4168 324/72 |
| 2013/0153443 A1 | 6/2013 | Nam |
| 2015/0303504 A1 | 10/2015 | Li |

OTHER PUBLICATIONS

Lyle Alexander, Written Opinion of the International Preliminary Report on Patentablity, PCT/US2017/038050, dated Nov. 26, 2018, pp. 1-20, IPEA/USPTO, Alexandria VA, USA.

* cited by examiner

*Primary Examiner* — Lore R Jarrett
(74) *Attorney, Agent, or Firm* — Rylander & Associates PC; Philip R. M. Hunt

(57) ABSTRACT

A method in which a concentration of a chemical species of interest is obtained. The method comprises measuring a property (e.g. the oxidation reduction potential) of a reagent (typically based on a simple single electron redox couple) to obtain a baseline measurement. The reagent is mixed with the solution under test, then the property of the mixture is measured to obtain a post reaction measurement. Then the concentration of the chemical species of interest is determined based on the baseline measurement and the first post reaction measurement, typically by calculating a difference of the baseline measurement and the post reaction measurement, then using the difference and a pre-determined conversion table to determine the concentration of the chemical species of interest.

19 Claims, 1 Drawing Sheet

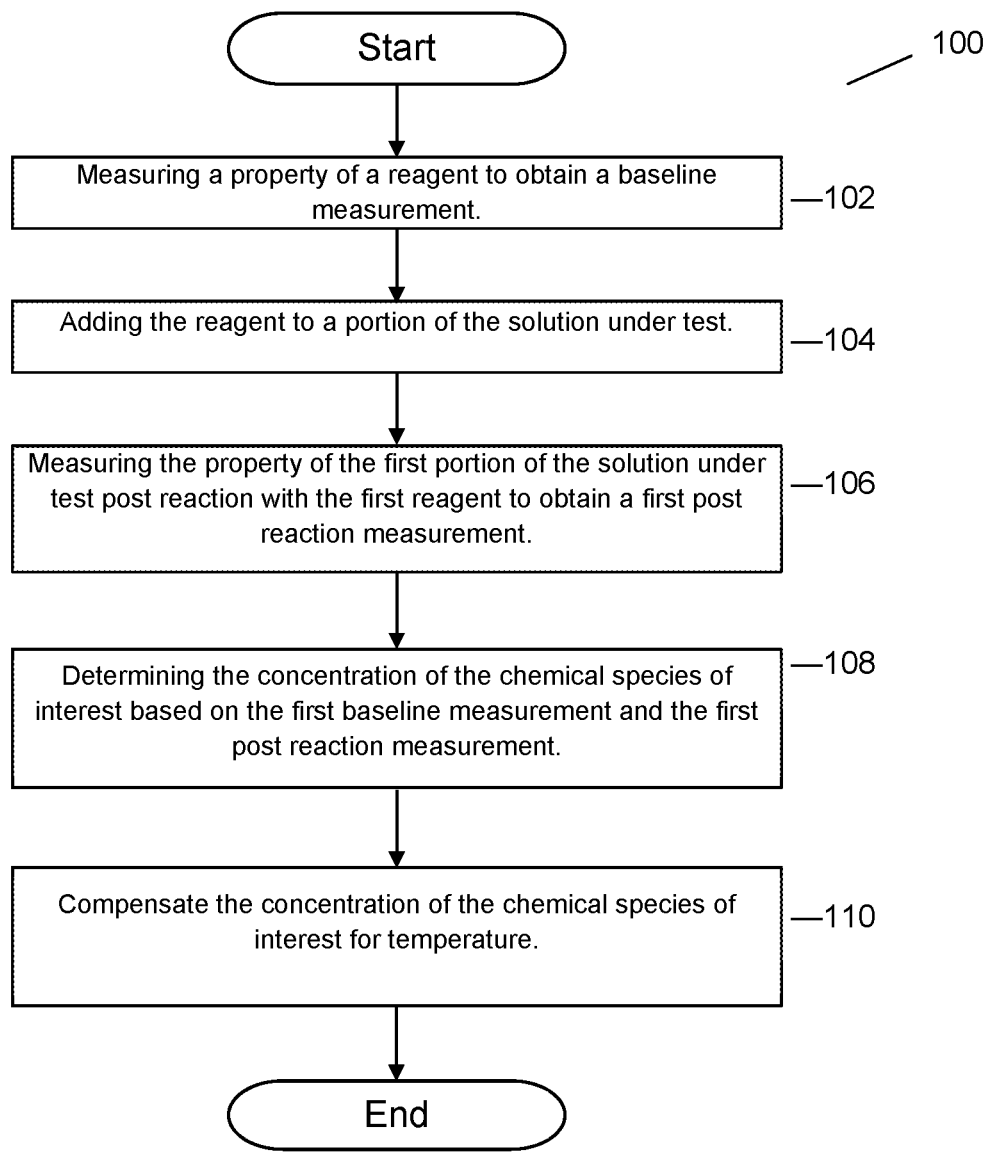

METHOD FOR MEASURING THE CONCENTRATION OF A CHEMICAL SPECIES USING A REAGENT BASELINE

CROSS-REFERENCE TO RELATED APPLICATIONS

This application claims the benefit of U.S. Provisional Application No. 62/351,671, filed 17 Jun. 2016, incorporated herein by reference.

TECHNICAL FIELD

This specification relates to methods and devices for measuring the concentration of a chemical species of interest. More particularly, the present specification relates methods and equipment for detecting an oxidizer in solution.

BACKGROUND

Reduction and oxidation reaction is a commonly utilized method to control or measure the concentration of a chemical species of interest. It is widely employed in process control in paper/pulp industry, sanitation control such as swimming pool and drinking water safety, and waste water management. A noble metal sensor, such as platinum and gold is the most commonly used sensor for providing such a measurement. This measurement is commonly known as the oxidation reduction potential (ORP) measurement.

Although generally effective, prior art ORP measurement methods suffer from slow response speed, uncertainty of which of chemical reaction from several that may be occurring gives rise to the oxidation reduction potential, and the lack of ability to distinguish sensor fouling or memory effect from the measurement of the species of interest. For example, a known redox process centering at the intended control point may provide an ORP value of 500 mV. However, if the sensor is fouled, then it is hard to tell the difference between a reading of 400 mV as the actual response or the sensor is fouled such that the reading is compromised. Since there is no other independent measurement to differentiate a fouled sensor versus a good sensor, the user can only assume the reading is a true indication of the reaction rate. Another example of the short comings of prior art methods, these methods can have slow response times when measuring the ORP of species in which the reaction measured involves a two-step electron transfer process. In prior art methods, there is no convenient way to tell if a slowly increasing response is caused by the sensor or by the complexity of the two electrons transfer process. Previously, there was no known method for those skilled in the art to overcome these challenges.

SUMMARY

The present invention provides a method in which a concentration (or the reaction rate) of a chemical species of interest is obtained. The method comprises measuring a property of a reagent to obtain a baseline measurement. The method continues with adding the reagent to the solution under test, then measuring the property of the solution under test post reaction with the first reagent to obtain a post reaction measurement, and then determining the concentration of the chemical species of interest based on the baseline measurement and the first post reaction measurement. Typically, this is done by calculating a difference of the baseline measurement and the post reaction measurement, then using the difference and a pre-determined conversion table to determine the concentration of the chemical species of interest.

A baseline measurement process effectively calibrates the sensor of the test instrument every time by using the reagent before reacting with the species of interest. This provides an unambiguous performance verification of the sensor. Furthermore, any offset in the sensor response is factored in every measurement of the species of interest.

The property measured may be an oxidation reduction potential (ORP), but could also be temperature, pH, conductivity, viscosity, turbidity, gas solubility, or color. The reagent may be based on a simple, single electron, redox couple, such as $Fe^{2+}$ and $Fe^{3+}$, but may be other reducing or oxidizing reagents.

Using a reagent based on a single electron redox couple provides a rapid response in an ORP measurement compared to a more complex redox process and the response time of the measurement is improved significantly. Furthermore, the instability of the chemical reaction is also being factored out as the simple redox couple will now be the dominant ORP indicator.

For example, the ferrous ($Fe^{2+}$) and ferric ($Fe^{3+}$) ions is a single electron redox couple with a readily reversible reaction. A reagent based on such a single electron redox couple may be used to measure the concentration of a more complex oxidizing reagent such as hypochlorous acid using an ORP measurement. Due to the single electron reversible conversion between $Fe^{2+}$ and $Fe^{3+}$, the ORP of the combined reagent and solution under test will reflect closer to the value predicted by Nernst equation, making the measurement more repeatable and reliable.

The surface of the noble metal in an ORP sensor, such as Pt and Au, can be poisoned when exposing to high ORP conditions. For example, with the chemistry system of OCl— and HOCl, at neutral pH, the oxidizing disinfectant can easily boost the ORP to above 700 mV even at low concentration, making the electrode "poisoned," leading to sluggish or even false readings. This poisoning can remain on the noble metal electrode, causing a "memory effect" when measuring subsequent species, leading to false measurements. When using the ferrous and ferric redox reagent, the ORP will be brought down to much lower values. This mitigates the "poisoning" and the "memory effect." The redox reagent concentration can also be adjusted to measure the oxidizing disinfectant in different ranges.

BRIEF DESCRIPTION OF THE DRAWINGS

The accompanying drawings, which are incorporated into and constitute a part of this specification, illustrate one or more embodiments of the inventive subject matter and, together with the detailed description, explain the principles and implementations thereof. Like reference numbers and characters are used to designate identical, corresponding, or similar components in different figures. The figures associated with this disclosure typically are not drawn with dimensional accuracy to scale, i.e., such drawings have been drafted with a focus on clarity of viewing and understanding rather than dimensional accuracy.

FIG. 1 is a flow chart of a representative embodiment of a method for measuring a concentration of a chemical species of interest in a solution under test.

DETAILED DESCRIPTION

In describing the one or more representative embodiments of the inventive subject matter, use of directional terms such as "upper," "lower," "above," "below", "in front of," "behind," etc., unless otherwise stated, are intended to describe the positions and/or orientations of various components relative to one another as shown in the various Figures and are not intended to impose limitations on any position and/or orientation of any component relative to any reference point external to the Figures.

In the interest of clarity, not all the routine features of representative embodiments of the inventive subject matter described herein are shown and described. It will, of course, be appreciated that in the development of any such actual implementation, numerous implementation-specific decisions must be made in order to achieve specific goals, such as compliance with application and business-related constraints, and that these specific goals will vary from one implementation to another and from one developer to another. Those skilled in the art will recognize that numerous modifications and changes may be made to the representative embodiment(s) without departing from the scope of the claims. It will, of course, be understood that modifications of the representative embodiments will be apparent to those skilled in the art, some being apparent only after study, others being matters of routine mechanical, chemical and electronic design. No single feature, function or property of the representative embodiments is essential. In addition to the embodiments described, other embodiments of the inventive subject matter are possible, their specific designs depending upon the particular application. As such, the scope of the inventive subject matter should not be limited by the particular embodiments herein described but should be defined only by the appended claims and equivalents thereof.

Representative Embodiment—Method

FIG. 1 shows a flow chart of a representative embodiment of a method 100 for measuring a concentration of a chemical species of interest in a solution under test. The solution under test is an aqueous solution of an oxidizer, such as chlorine. Water from a swimming pool or domestic water supply would be typical sources.

The method 100 uses a test instrument that can measure oxidation reduction potential (ORP), temperature, and pH. In other embodiments, the test instrument measures conductivity and/or some other property. The instrument is configured with a sensor well to hold the solution under test. The measurements and the overall method are controlled by an embedded microcontroller, with some user input.

The representative embodiment method 100 uses a reagent based on a redox couple. The reagent will reduce any oxidizer in the sample solution. In the representative embodiment, the reagent is based on a redox couple of $Fe^{2+}$ and $Fe^{3+}$.

The first step of the representative embodiment method 100 is a baseline measurement step 102. The baseline measurement step 102 comprises measuring a property of the reagent to obtain a baseline measurement. This baseline measurement step 102 begins with the sub-steps of rinsing the sensor well with the reagent, then filling the sensor well with the reagent. The baseline measurement step then continues with the sub-steps of measuring the oxidation reduction potential (ORP) of the reagent (typically in millivolt (mV)), then recording this ORP measurement as a baseline measurement. The baseline measurement step 102 then ends with emptying the sensor well.

The second step is a sample pretreatment step 104. The sample pretreatment step 104 comprises adding a first reagent to the solution under test. This sample pretreatment step 104 begins with the sub-step of measuring out a pretreatment amount of the sample solution, sufficient to fill the senor well (about 25 ml). The sample pretreatment step 104 then continues with the sub-step of adding an amount of a selection agent, sufficient to make the pretreatment amount of the sample solution have a pH in the range of 2.0-3.0, resulting in a pretreated sample solution. In the representative embodiment, the selection agent is 0.09N Sulfuric Acid, but other reagents and concentrations may be used. This step removes interference species, such as forms of bicarbonate species ($NaHCO_3$, $HCO_3^-$).

The third step is a sample measurement step 106. The sample measurement step 106 comprises measuring the property of the solution under test post reaction with the reagent to obtain a post reaction measurement. The sample measurement step 106 begins with the sub-step of adding a quantity of the reagent to the pretreated sample solution in a ratio predetermined to be sufficient for accelerating the measurement process. In the representative embodiment, a ratio of 6 to 1 (e.g. 15 ml to 2.5 ml) is used, but in other embodiments, other ratios may be used. The sample measurement step 106 then continues with the sub-steps of mixing the pretreated sample solution and reagent for sufficient time to produce a mixture solution, then allowing the mixture solution for sufficient time to stabilize. In the representative embodiment, the pretreated sample solution and reagent are mixed for 1 minute, and the mixture solution is allowed to stabilize for 1 minute, but other times may be used in other embodiments of the method for other species of interest and reagents. The sample measurement step 106 then continues with the sub-steps of rinsing the sensor well with the mixture solution (typically filling and emptying three times), filling the sensor well with the mixture solution, then measuring the ORP of mixture solution (typically in mV), then recording the measurement as the post reaction measurement.

The fourth step is a conversion step 108. The conversion step 108 comprises determining the concentration of the chemical species of interest based on the baseline measurement and the post reaction measurement. The conversion step 108 uses a conversion table with two sets of related values. The table is generated in advance, typically in a laboratory, cross-checking the values with higher sensitivity equipment. The first set of values are property measurement values (ORP values in the first embodiment, typically in mV) and the second set of values is concentration of the species of interest (typically in parts per million (ppm)). Each of the property measurement values is associated with one of the concentration values. The conversion step 108 begins with calculating a delta-measurement value based on a difference between the baseline measurement and the post reaction measurement. The conversion step 108 then continues with obtaining concentration of the chemical species of interest in the solution under test by using the delta-measurement value to obtain an associated concentration value from the conversion table, which is designated as the (uncompensated) concentration of the chemical species of interest.

The fifth step is a temperature compensation step 110. The temperature conversion step 110 begins with measuring the temperature of the mixture solution. This is followed by determining the (compensated) concentration of the chemical species of interest based on the (uncompensated) concentration of the chemical species of interest (determined in the conversion step) and the temperature. The compensated concentration is the value corrected to standard temperature, typically 25° C. In the first exemplary method, a temperature compensation formula is used, but in other embodiments, a table may be used. The temperature conversion step 110 continues with presenting the compensated concentration of the chemical species of interest, typically by displaying it on an electronic display. The temperature conversion step 110 ends with accepting a final compensated concentration of the chemical species of interest after 30-45 seconds or when the value of the compensated concentration stabilizes.

What is claimed is:

1. A method for measuring a concentration of a chemical species of interest in a solution under test utilizing an instrument with a sensor well to hold the solution under test, comprising the following steps in the order recited:
    filling the sensor well with a first reagent;
    measuring a property of first reagent to obtain a first baseline measurement, wherein the first reagent is based on a redox couple that utilizes a single electron transfer process;
    emptying the sensor well;
    producing a first mixture solution by adding a quantity of the first reagent to a first portion of the solution under test;
    filling the sensor well with the mixture solution;
    measuring the property of the first mixture solution to obtain a first post reaction measurement; and
    determining the concentration of the chemical species of interest based on the first baseline measurement and the first post reaction measurement.

2. The method of claim 1,
    wherein the property is one of a group of temperature, pH, oxidation reduction potential, conductivity, viscosity, turbidity, gas solubility, and color.

3. The method of claim 1, wherein the property is oxidation reduction potential.

4. The method of claim 1, wherein the quantity of the first reagent added in producing the mixture solution is sufficient for accelerating the measuring of the property of the first mixture solution.

5. The method of claim 1, wherein the first reagent is based on a redox couple that utilizes a single electron transfer process with a readily reversible reaction.

6. The method of claim 1, wherein the first reagent is based on a redox couple of $Fe^{2+}$ and $Fe^{3+}$.

7. The method of claim 1,
    wherein determining the concentration of the chemical species of interest utilizes a conversion table with two sets of related values, including a first set comprising property measurement values and a second set comprising concentrations of the species of interest, each value of the first set associated with one of the values of the second set.

8. The method of claim 1, further comprising:
    after producing the first mixture, allowing the first mixture solution sufficient time to stabilize.

9. The method of claim 1, 2, 3, 4, 5 or 6, wherein determining the concentration of the chemical species of interest further comprises:
    calculating a difference of the first baseline measurement and the first post-reaction measurement; and
    using the difference and a conversion table to determine the concentration of the chemical species of interest.

10. The method of claim 1, further comprising after the steps of claim 1, the following steps in the order recited:
    filling the sensor well with a second reagent,
    measuring a property of the second reagent to obtain a second baseline measurement, wherein the second reagent is based on a redox couple that utilizes a single electron transfer process;
    emptying the sensor well;
    creating a second mixture solution by adding a second reagent to a second portion of the solution under test;
    measuring the property of the second mixture solution to obtain a second post-reaction measurement; and
    determining the concentration of the chemical species of interest based on the first baseline measurement, the first post reaction measurement, the second baseline measurement, and the second post reaction measurement.

11. The method of claim 10,
    wherein said second reagent is based on a redox couple that utilizes a single electron transfer process with a readily reversible reaction.

12. The method of claim 10, wherein determining the concentration of the chemical species of interest further comprises:
    calculating a first difference value based on a difference of the first baseline measurement and the first post-reaction measurement;
    calculating a second difference value based on a difference of the second baseline measurement and the second post reaction measurement; and
    using the first difference value, the second difference value and conversion table to determine the concentration of the chemical species of interest.

13. A method for measuring a concentration of a chemical species of interest in a solution-under-test, comprising the following steps in the order recited:
    measuring an oxidation reduction potential (ORP) of a reagent to obtain a baseline measurement;
    wherein said reagent is based on a redox couple that utilizes a single electron transfer process;
    adding the reagent to a portion of the solution under test;
    measuring the ORP of the portion of the solution under test post-reaction with the reagent to obtain a post-reaction measurement;
    calculating a difference of the baseline measurement and the post-reaction measurement; and
    using the difference and a conversion table to determine the concentration of the chemical species of interest.

14. The method of claim 13,
    wherein said reagent is based on a redox couple of $Fe^{2+}$ and $Fe^{3+}$.

15. A method for measuring a reaction rate of a chemical species of interest in a solution-under-test utilizing an instrument with a sensor well to hold the solution under test, comprising the following steps in the order recited:
    filling the sensor well with a first reagent;
    measuring a property of a first reagent to obtain a first baseline measurement, wherein the first reagent is based on a redox couple that utilizes a single electron transfer process;
    emptying the sensor well;
    producing a first mixture solution by adding a quantity of the first reagent to a first portion of the solution-under-test;
    filling the sensor well with the first mixture solution;
    measuring the property of the first mixture solution to obtain a first post-reaction measurement; and
    determining the reaction rate of the chemical species of interest based on the first baseline measurement and the first post-reaction measurement.

16. The method of claim 15, wherein the property is one of a group of temperature, pH, oxidation reduction potential, conductivity, viscosity, turbidity, gas solubility, and color.

17. The method of claim 15, wherein the property is oxidation reduction potential.

18. The method of claim 17, wherein the first reagent has a rapid response in an ORP measurement.

19. The method of claim 15, 16, 17, or 18, wherein determining the reaction rate of the chemical species of interest further comprises:

calculating a difference of the first baseline measurement and the first post-reaction measurement; and using the difference and a conversion table to determine the reaction rate of the chemical species of interest.

* * * * *